(12) United States Patent
Weissman

(10) Patent No.: US 7,431,589 B2
(45) Date of Patent: Oct. 7, 2008

(54) COMPONENTS FOR PERMANENT REMOVABLE AND ADJUSTABLE DENTURES AND BRIDGES

(76) Inventor: Bernard Weissman, 225 E. 48th St., New York, NY (US) 10017

( * ) Notice: Subject to any disclaimer, the term of this patent is extended or adjusted under 35 U.S.C. 154(b) by 0 days.

(21) Appl. No.: 11/419,801

(22) Filed: May 23, 2006

(65) Prior Publication Data
US 2006/0269902 A1 Nov. 30, 2006

Related U.S. Application Data

(60) Provisional application No. 60/685,640, filed on May 27, 2005.

(51) Int. Cl.
*A61C 8/00* (2006.01)
(52) U.S. Cl. .................................................. 433/174
(58) Field of Classification Search .......... 433/172–174
See application file for complete search history.

(56) References Cited

U.S. PATENT DOCUMENTS

| | | | |
|---|---|---|---|
| 711,324 A | 10/1902 | Lacy | |
| 1,101,810 A | 6/1914 | Otrich et al. | |
| 2,112,007 A | 3/1938 | Pinkney | |
| 3,085,334 A | 4/1963 | Bischof et al. | |
| 3,514,858 A | 6/1970 | Silverman | |
| 3,656,236 A | 4/1972 | Kurer | |
| 3,748,739 A | 7/1973 | Thibert | |
| 4,204,321 A | 5/1980 | Scott | |
| 4,253,834 A | 3/1981 | Staubli | |
| 4,290,755 A | 9/1981 | Scott | |
| 4,459,111 A | 7/1984 | Valen | |
| 4,516,937 A | 5/1985 | Bosker | |
| 4,654,006 A | 3/1987 | Kusano et al. | |
| 4,787,851 A | 11/1988 | Kusano et al. | |
| 4,854,872 A | 8/1989 | Detsch | |
| 4,968,250 A * | 11/1990 | Small .......................... 433/173 |
| 5,052,928 A | 10/1991 | Andersson | |
| 5,052,930 A | 10/1991 | Lodde et al. | |
| 5,064,374 A | 11/1991 | Lundgren | |
| 5,194,000 A | 3/1993 | Dury | |
| 5,427,906 A | 6/1995 | Hansen | |
| 5,487,664 A | 1/1996 | Weissman | |

(Continued)

FOREIGN PATENT DOCUMENTS

WO 02/04276 A1 1/2002

(Continued)

*Primary Examiner*—Ralph A Lewis
(74) *Attorney, Agent, or Firm*—Paul J. Sutton; Barry G. Magidoff

(57) ABSTRACT

A dental prosthesis foundation capable of being finished or adjusted or repaired and which may be assembled and adjusted to variable jaw ridge sizes, and formed with self-curing hardened resins. The foundation supports prosthetic teeth and is permanently but removably secured to the jaw by implants embedded in hard dental tissue, such as tooth stubs or bones. The dentures can be readily repaired or adjusted for changes in the jaw of the patient, by chairside techniques available to dentists. The foundation can also be adjusted to changes in size and shape of ridges in the jawbones for more comfortable use of the dentures secured on such prostheses, by utilizing spheroidal or ovoidal locking caps preferably initially formed of non-adherent polymers.

7 Claims, 22 Drawing Sheets

U.S. PATENT DOCUMENTS

| | | |
|---|---|---|
| 5,513,988 A | 5/1996 | Jeffer et al. |
| 5,520,540 A | 5/1996 | Nardi et al. |
| 5,538,428 A | 7/1996 | Staubli |
| 5,567,155 A | 10/1996 | Hansen |
| 5,575,651 A | 11/1996 | Weissman |
| 5,597,306 A | 1/1997 | Horlitz et al. |
| 5,678,993 A | 10/1997 | Jeffer et al. |
| 5,725,376 A | 3/1998 | Poirier |
| 5,788,492 A | 8/1998 | Weissman |
| 5,871,357 A | 2/1999 | Tseng |
| 5,885,077 A | 3/1999 | Jeffer |
| 5,944,529 A | 8/1999 | Rappold |
| 6,068,479 A | 5/2000 | Kwan |
| 6,382,975 B1 | 5/2002 | Poirier |
| 6,575,742 B2 | 6/2003 | Kyung et al. |
| 6,685,473 B2 | 2/2004 | Weissman |
| 6,716,030 B1 | 4/2004 | Bulard et al. |
| 2005/0014108 A1 | 1/2005 | Wohrle |

FOREIGN PATENT DOCUMENTS

| | | |
|---|---|---|
| WO | WO 02/28304 A2 | 4/2002 |
| WO | WO 2004/060189 A2 | 7/2004 |

\* cited by examiner

COMPONENTS FOR PERMANENT REMOVABLE AND ADJUSTABLE DENTURES AND BRIDGES

This application claims the benefit of the filing date of provisional application having Ser. No. 60/685,640, which was filed on May 27, 2005 and U.S. pending patent application Ser. No. 10/746,674, which was filed on Dec. 24, 2003.

FIELD OF THE INVENTION

The present invention relates to further improvements in dental implant structures, and in particular to adjustable and/or modular, removably secured dentures and dental bridges, i.e., oral, or dental prosthetics. A detailed background for this invention is provided in related International Publication number WO 02/28304 A2, published on 11 Apr. 2002 (hereinafter the "Prior Case) and number WO2004/060189 A3, (hereinafter the "Prior Case II"), by the same inventor and applicant, the complete disclosures of which are incorporated herein by reference, including the specification and drawings.

BACKGROUND OF THE INVENTION

As shown in FIG. 1 of the Prior Cases, it is well known to firmly attach dentures to hard dental tissue, such as the jawbone 14 or tooth stubs by an implanted support, via prosthetic dental bridges 10; foundations 12 for such bridges 10 are known. In particular, the dental bridge 10 may be securely mounted to implanted screw posts 16, or other known securing mechanisms. Such foundations 12 are also described, for example, in U.S. Pat. Nos. 5,575,651 and 5,788,492. Other, more readily removable, dentures secured to implanted supports are shown, for example in U.S. Pat. Nos. 5,567,155 and 3,514,858.

The use of relatively slender implants to support foundations, described in the first two patents identified above, and in the Prior Cases, were originally considered suitable primarily as short term devices for use until the larger, "permanent" implants healed. One aspect of the present invention continues the earlier development and further understanding that the slim implants can be used for substantially permanent, but removable denture prostheses of various types. The devices and procedures of the present invention avoid many of the problems of earlier systems when worn for extended periods, which included the lack of capability for easy removal and replacement, and potential irritation to the patient because of the difficulty of obtaining a proper fit to the jawbone and opposing teeth and gums, or to soft dental tissue.

Thus, a need continued to exist for a system which would permit the placement of a long-lasting dental prosthesis in a patient's mouth by chairside techniques available to the family dentist. Such a system should provide components for mounting such prosthesis, which can be firmly secured to the hard dental tissue, such as the jawbone, in a relatively short time, but which can be adjusted or removed to be prophylactically cleaned or repaired at a later date, and which are readily adaptable to the natural variations in the size and shape of ridges in jaw bones, so as to provide for more comfortable use of any dentures secured on such components, and which allows for multiple fittings and adjustments without damage to even the slender implants.

SUMMARY OF THE INVENTION

In accordance with a first aspect of the present invention, The existing or new denture prosthesis can be retrofitted with the advantageous system of this invention. The prosthesis can be removed from the mouth by the patient to be prophylactically cleaned daily, but is primarily is intended for fitting or refitting of the prosthesis without damage to the implant posts, by the dentist.

The improvement of this invention is to be primarily used in denture systems comprising anchoring implants and indexing guide pins that are permanently implanted, bi-laterally, at the most posterior parts of the jaw. The channel forming the concave underside of a full, or partial, denture, for either the upper or lower jaw, can be lined with a resilient material, covering the hard denture form, and thus more effectively maintain the denture in the correct position while cushioning the patient's dental ridge. Such a denture lining is intended to provide for an improved grip on implants, and can be readily resurfaced.

A chairside prosthesis foundation is also provided for securing to a plurality of anchored dental implants, in accordance with the Prior Cases. Each implant useful in that situation has an intermediate platform portion and an interconnectable top distal from the, preferably threaded, implanted portion. The foundation can comprise modular components, which can be supported by the intermediate implant platforms, but which can be locked together by being encased in a resin, in a permanent relative juxtaposition. The locked together components can be removably connected to the implants, to enable subsequent adjustment of the prosthesis to fit a range of jaw ridge sizes or for cleaning or repair. As explained in the Prior Cases, such modular components are secured in the jaw efficiently and relatively easily, and can be adjusted at a later date, to conform to the many variations in the size or shape of ridges in the jaw, rendering the prostheses more comfortable to the wearer. As also explained in the Prior Cases, the modular components can be interconnected while secured to the implants and are then reinforced and locked together by being encased by a cured, or hardened, resin composition, such as any of the self-curing dental resins well known to dentists.

Both types of foundations, each referred to as a "splint", provides a base upon which tooth forms/synthetic teeth can be supported. When the screw shafts are implanted, temporary tooth forms can be created at chairside by a dentist, once a splint is in place, to provide a patient with a prompt replacement of missing teeth, which are firmly but replaceably connected to the implants. Immediately after placing the implants, the splint serves to index the implanted screws so that they are maintained in position without movement, to aid in the healing process with the jawbone, by allowing the bone to firmly grow around the implants.

In one embodiment, shown in the Prior Case and Prior Case II, each implant shaft has a polygonal top driving portion, engaging an indexing member which fits around and is held in a desired juxtaposition by the polygonal top. The preferred indexing member has paired arms extending outwardly therefrom, forming slots there between. Connecting bars, or flexible bands, extend through the slots on each indexing member from the first of a series of such implants to the last of the series, thus interconnecting the indexing members and thus anchoring the group of implanted screws together, to support each other in the desired juxtaposition. Each indexing member is in turn releasably secured to its respective implant shaft by a locking cap. To further enhance the rigidity and support provided by the overall splint structure, the bars and the indexing members are encased in a resinous material, thus forming a unitary rigid structure, which can be separated as a unit from the series of implants.

In accordance with the improvement of the present invention, by forming the locking caps from a material which is relatively soft compound to the implant posts, and non-adherent to the encasing dental resin, such as silicone or other polymeric non-adherent material, such as the polyacetal Delrin, the locking cap can be readily and safely unscrewed from the implant, so that the foundation splint structure can be removed from the implants, once the implants are firmly set, i.e., fully healed to the bone, or earlier, if necessary. Any of the temporary or longer term dentures can be thus supported on, and connected to the splint. The retaining implants as improved by this invention, preferably have a spheroidal head or an ovoidal head, extending above the gum line, and a platform substantially at the gum line and connected to the spheroidal or ovoidal head by a slender neck. A spheroidal head is one having a generally circular shape from a top view, and an ovoidal head is one having a generally elongated, or ellipsoidal, shape from a top view.

The ovoidal head allows a secure fit for dentures for use on patients having very narrow, so-called "knife-edge", gum ridges. The concavity on the inner surface of the dentures for such patients must be molded to have an especially narrow opening in order to obtain a firm fit over such narrow gum ridges. The use of the ovoidal head on the implants permits firm and secure fitting for even the narrowest ridge, by aligning the major axis of the ovoidial head with the ridge. Alternatively, a denture for a wider ridge may be equally firmly supported by aligning the ovoidal head transversely, or perpendicularly, to the gum ridge. This allows the ovoidal head to extend fully across even the widest denture concavity and provide the required firm support. The widest dentures would be supported by aligning the major axis perpendicularly to the gum ridge, thus, the ovoidal head provides the most versatile use covering a wide range of denture sizes.

In accordance with the invention, damage during removal of the locking caps is further eased, while lessening the possibility of unduly stressing or damaging the implant foundation, during the initial fitting period. In this invention, the non-adherent locking cap is formed of a polymer and has a skirt portion at one end, and a dome-shaped portion at another end, having a spheroidal or ovoidal shape. The skirt portion is preferably an annulus, concentric with the dome portion, and having an internal diameter sufficient to surround any elements secured on the intermediate platform, but not greater than that of the platform diameter, so that the skirt bottom presses against the top surface of the platform. Preferably, a non-circular or polygonal, top driving portion is supported on the platform and in turn supports the threaded connector. Most preferably, at best, two elongated circumferential apertures are provided through the skirt, with relatively narrow skirt wall portions separating the two apertures. The apertures are preferably symmetrical about the circumference. These non-adherent locking caps are especially useful during the initial fitting period, when the fittings and these caps must be removed from the implants several times.

The locking cap is threadedly secured to the interconnectable top of the implant. When fitting the locking cap onto an implant, the externally threaded interconnectable top mates with the internal threaded portion of the cap. To reduce the chances of unintentional loosening of the cap, the cap is locked in place using a curable resin, which is inserted into the internal space within the skirt annulus in the locking cap. The resin is preferably one that will cure and harden quickly after the cap is screwed onto the implant, and is non-adherent to the locking cap. This hardened resin, portions of which extend into the apertures, will further secure the locking cap from rotational movement, which might otherwise cause it to loosen by surrounding, for example, the polygonal driving portion. The resin can be selected from among common curable dental resins, such as a polyacrylic or an epoxy polymer. When the locking cap is to be removed, the usual torque level is applied by the driving tool; the hardened resin in the apertures will tear the narrow strips of polymer forming the intermediate strips between the apertures, when the torque is applied to the caps. These resins may be auto-curing or light-curing, both of which are commonly used in dentistry. Generally, these are non-adherent to many dental polymers, such as Delrin.

By providing cured resin through the apertures, the cap is locked in place, but the cap can be readily torn at the ends of the apertures, under applied torque, thus, removing the lock without dislodging or moving the implant part before healing is complete. The material between the apertures can be made more likely to split in response to an applied torque by reducing the cross-sectional thickness of the material at those intermediate portions. Preferably the apertures extend, in toto, at least about 50% of the circumference, and most preferably at least about 80% of the circumference. To avoid extrusion of the resin beyond the apertures, before hardening, a thin, non adherent sleeve can be placed over the apertures and around the skirt portion. The sleeve can hold the resin in place during curing. The sleeve is most preferably non-adherent to the resin filling in the cap, such as a silicone, and also can have a slight elasticity to improve holding and simplify removal after hardening.

In use, an auto-cure or light-cure resin is inserted into the inner cup of the skirt of the locking cap. The cap is firmly tightened in place utilizing a U-shaped driver which fits within the aperture in the locking cap. Preferably, the apertures extend around and down the sides of the cap, and the U-shaped driver can conform to the downwardly extending side slots. Alternatively, a standard straight or cruciform slot across the top of the dome is provided, to allow a screwdriver to be used, or a polygonal indentation, for use, for example by an Allen wrench-type of driver. As the cap is screwed down, any excess curable resin material is forced outwardly, or upwardly, out of the cap, and can be easily wiped away before the resin hardens. A silicone sleeve placed around the apertures can be removed after the resin hardens.

The locking cap thus is held against rotation by the hardened resin surrounding the polygonal driver part on the implant and extending into the apertures of the skirt portion. The lower skirt portion, between the apertures, can be lifted out, or broken-up when exposed.

When it is desired to remove the cap, by applying sufficient torque to the caps e.g. with the U-shaped driver in matching slots, the hardened resin in the skirt will fracture the skirt wall portions, separating the apertures allowing, and the internally threaded portion of the cap and the skirt will separate at the apertures, allowing it to be easily unscrewed from the implant.

During the healing period, an interim prosthesis lined with the silicone material serves to lock the implants in place while providing an interim tooth replacement for the patient. That interim prosthesis will be removed once healing is complete. This procedure may need to be repeated a number of times during the healing, and the following trials and fittings of the final customized prosthesis. This final prosthesis can be constructed with the components described in, for example, U.S. Pat. No. 6,685,473 B2. After removal of the cap with the separated bottom section, a new cap must be secured in place in the same manner, when the interim prosthesis is replaced after the fitting.

The non-adhesive locking cap of this invention, is especially useful during the repeated fitting operations, because it is far less likely to stress or damage the thread of the, e.g., titanium, implant when being installed onto the implant, or being removed therefrom.

In a preferred embodiment, a central opening extends through the cap, regardless of the shape of the head, so that it is open at both ends; this permits excess resin to escape out the top, as the cap is being screwed down, while being held in place onto the threaded portion. This central opening can be provided regardless of the shape of the cap head.

DETAILED DESCRIPTION OF THE PREFERRED EMBODIMENTS

Figure 1:
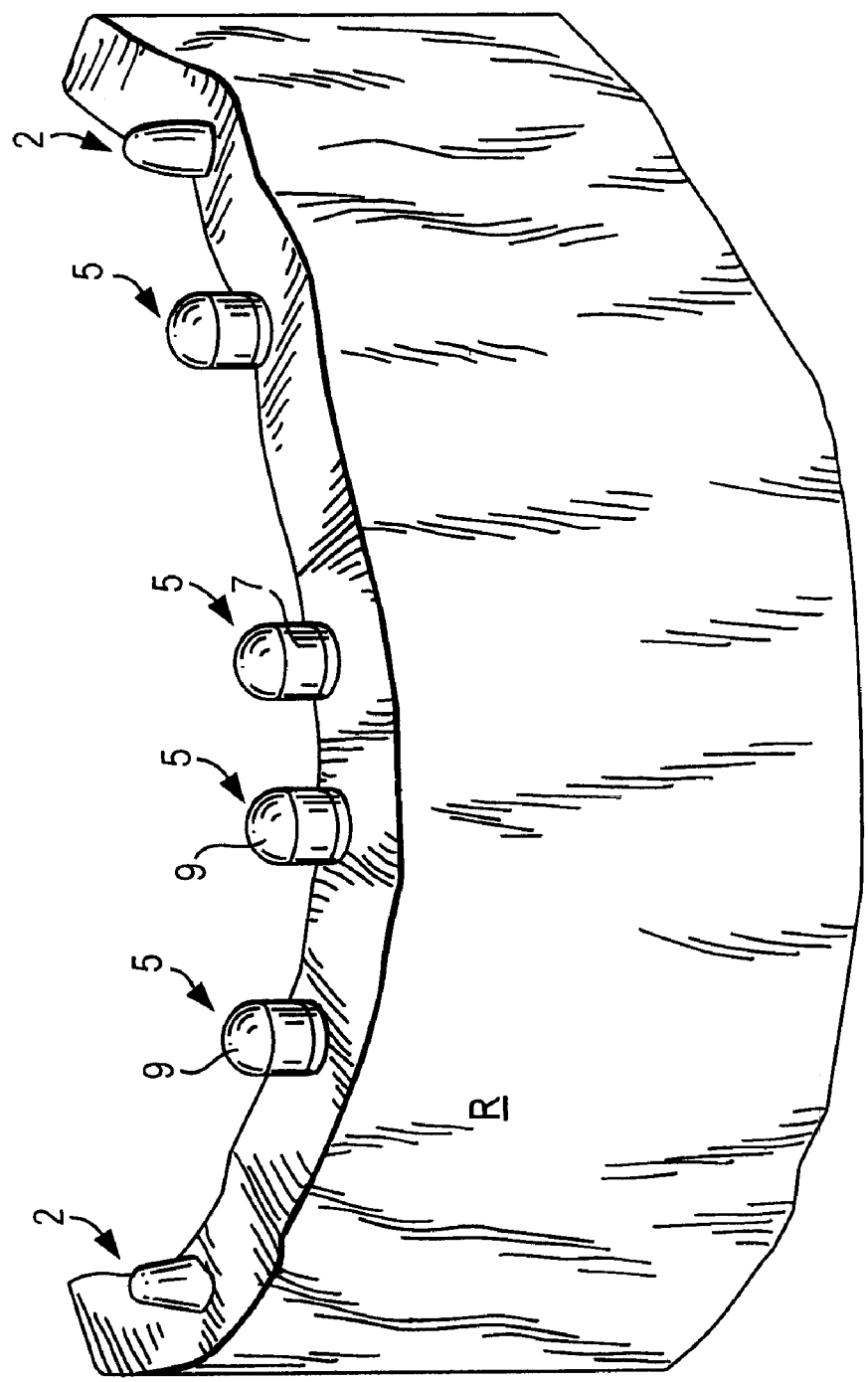
FIG. 1 illustrates, on a jaw model, a series of indexing and holding implants having the desired spheroidal head of this invention and banded necks.

As described herein, the various rigid structural components shown in the drawings are fabricated from, for example, titanium, stainless steel, and/or any other suitable dental implant material which can withstand functional loads and support crowns, bridge segments, or the complete replacement of teeth with tooth forms/synthetic teeth/artificial teeth.

Figure 1A:
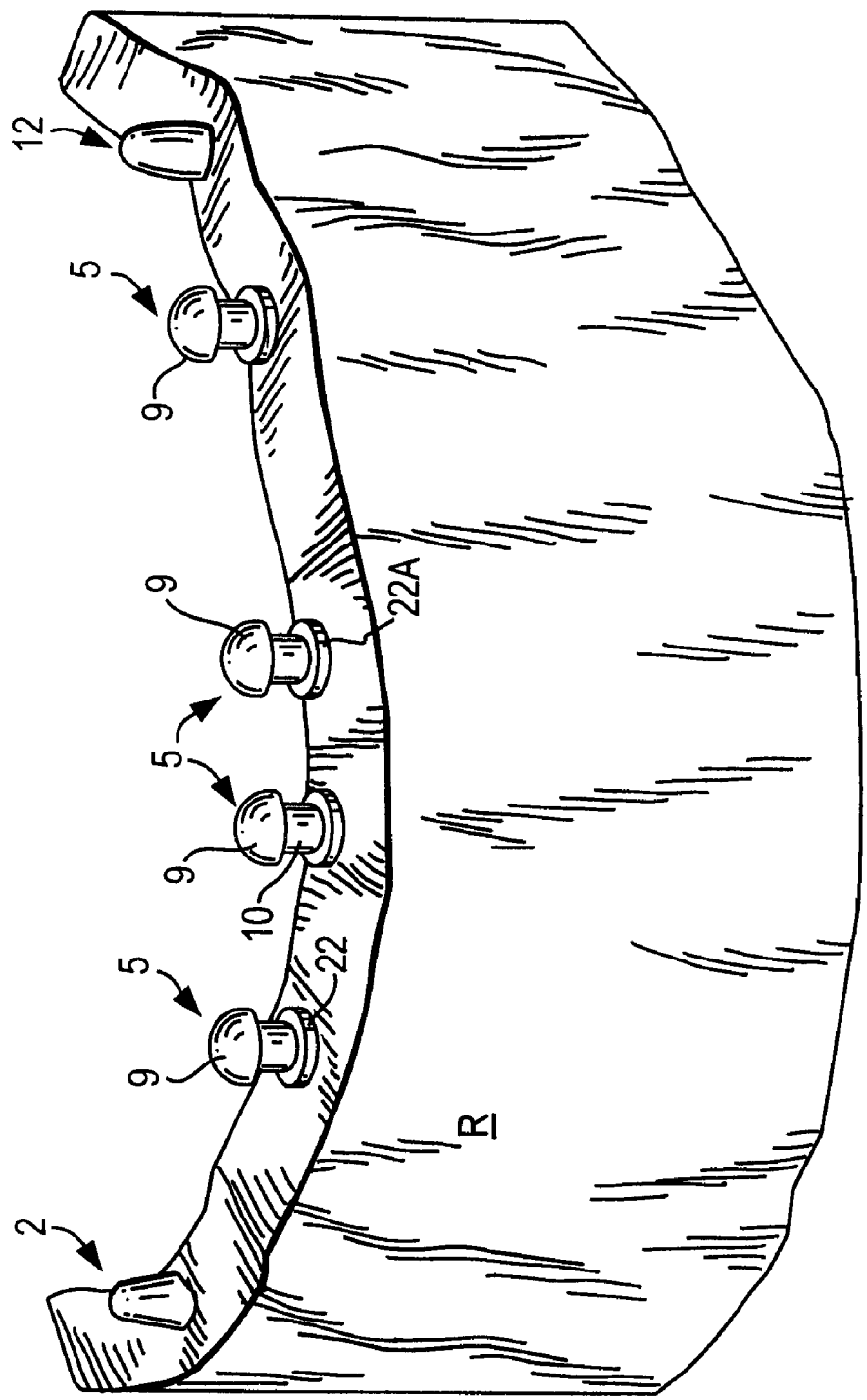
FIG. 1a illustrates, on the jaw model of FIG. 1, a series of indexing and holding implants having the desired spheroidal head of this invention without the neck bands.
Figure 2:
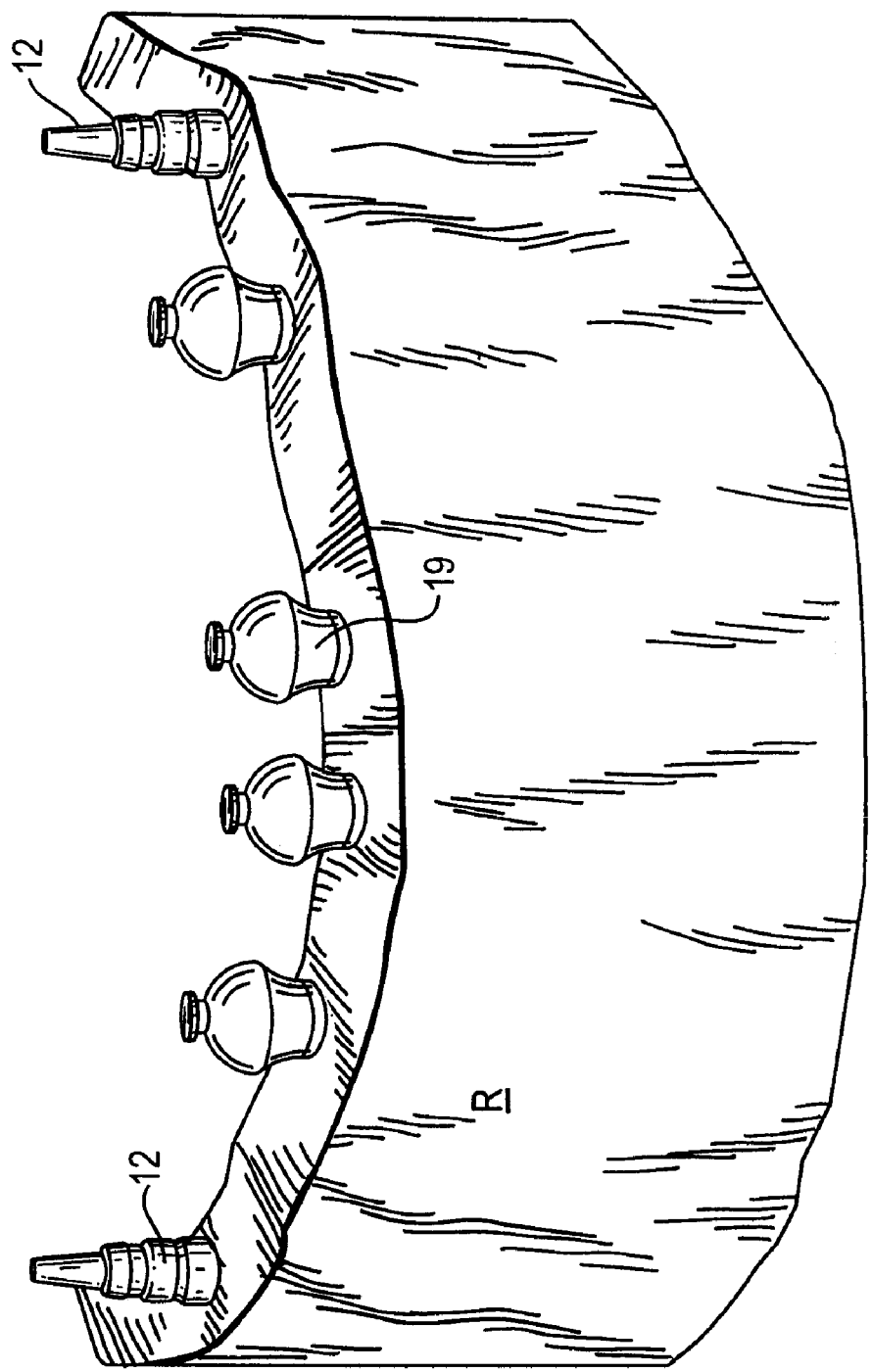
FIG. 2 illustrates, the jaw model of FIG. 1 with insert covers over the indexing implants.
Figure 3:
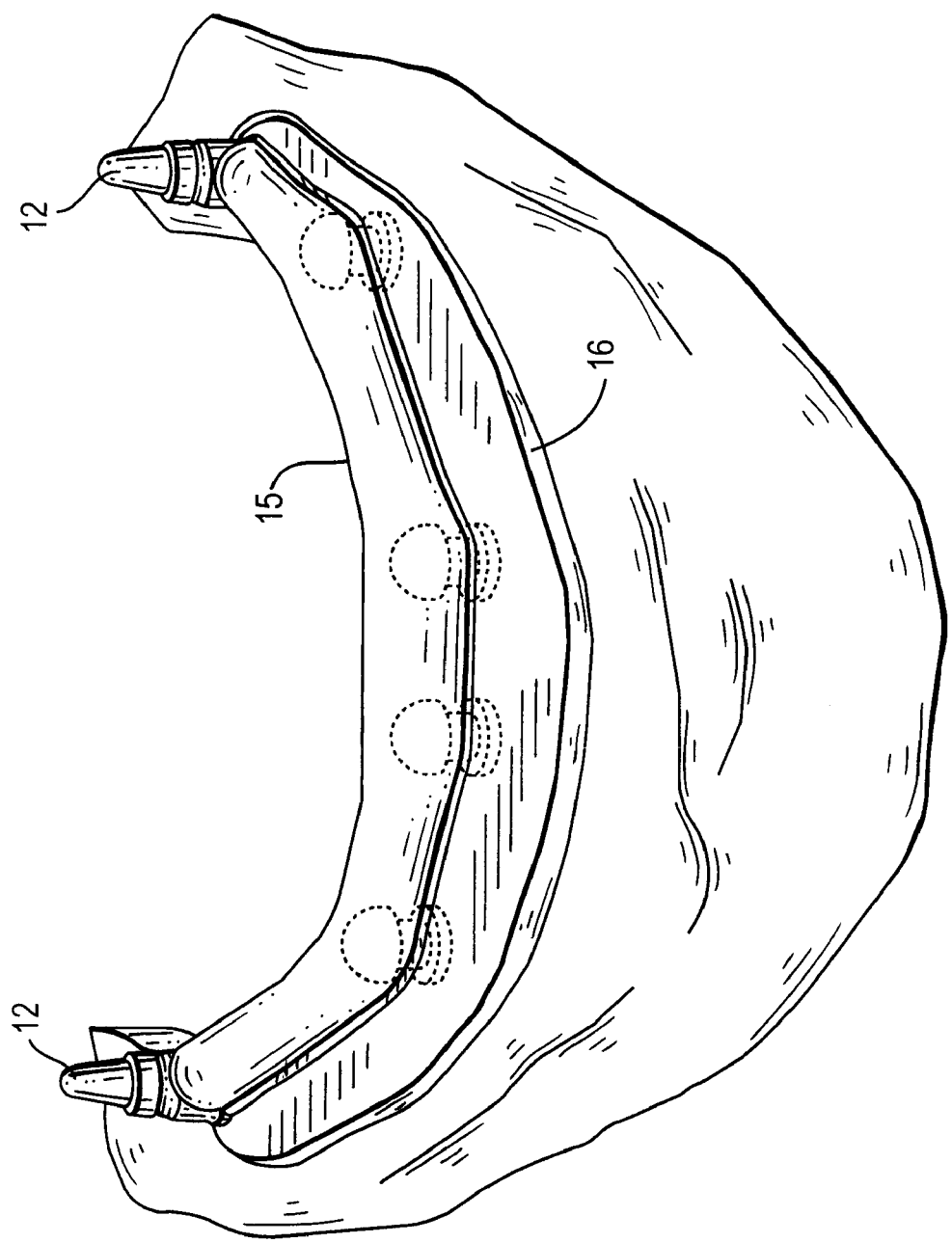
FIG. 3 illustrates, the jaw model of FIG. 1; wherein the holding implants are covered by a half sheath.
Figure 4:
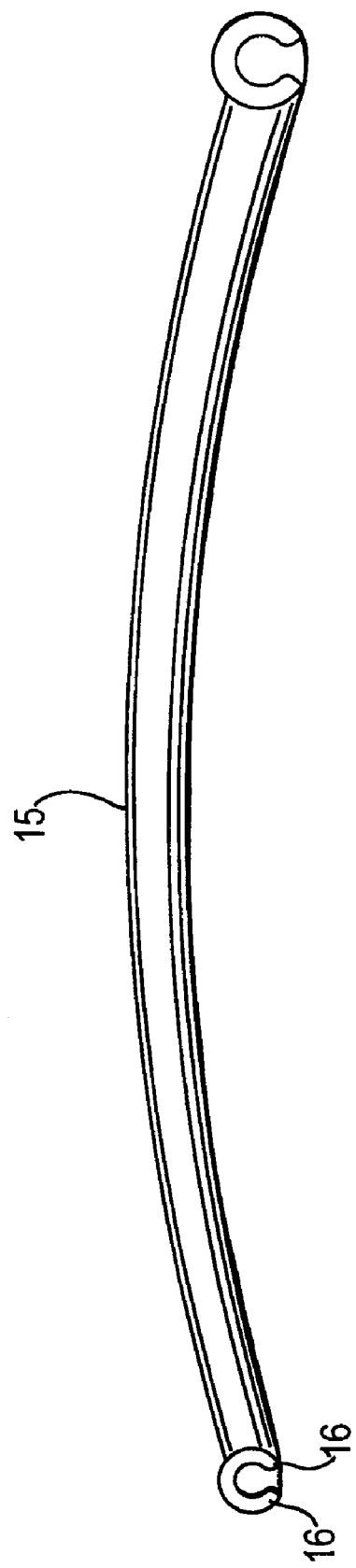
FIG. 4 illustrates a detailed perspective view of the half sheath shown in FIG. 3.
Figure 6:
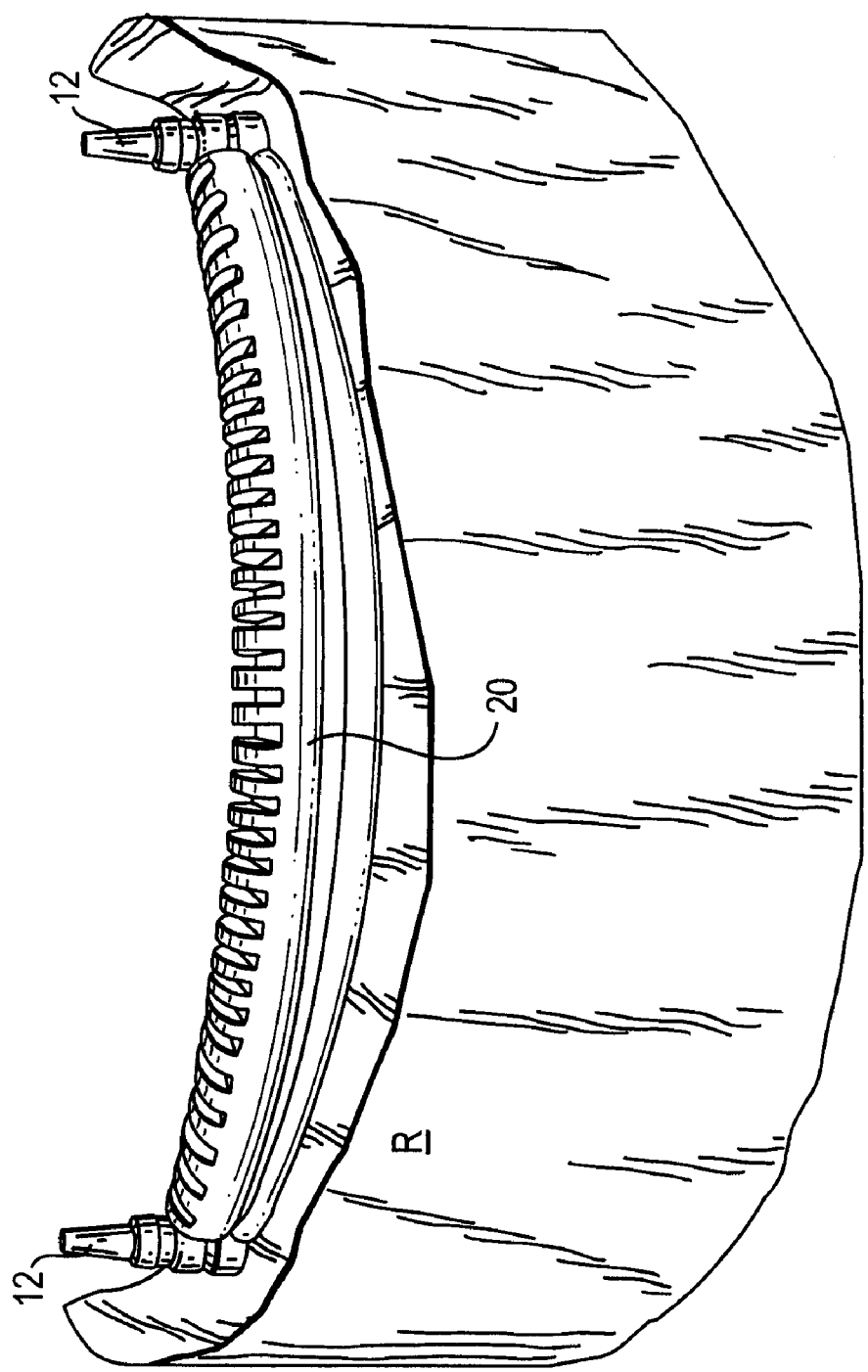
FIG. 6 illustrates, the jaw model of FIG. 3, wherein the holding implants are covered by a half sheath which is in turn covered by a metal reinforcing frame.
Figure 10:
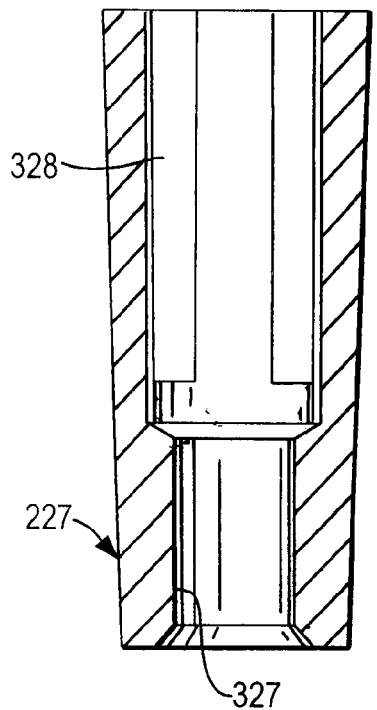
FIG. 10 illustrates a locking screw cap made of a structural, nonadherent polymer, such as the polyacetal Delrin, to secure the prosthesis to the implant.
Figure 5:
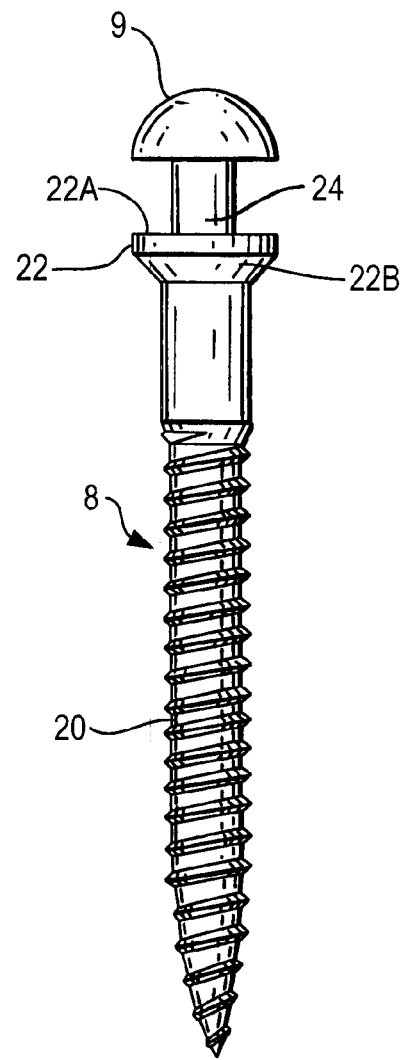
FIG. 5 illustrates a top plan view of the spheroidal head of the holding implants of FIG. 1.
Figure 7:
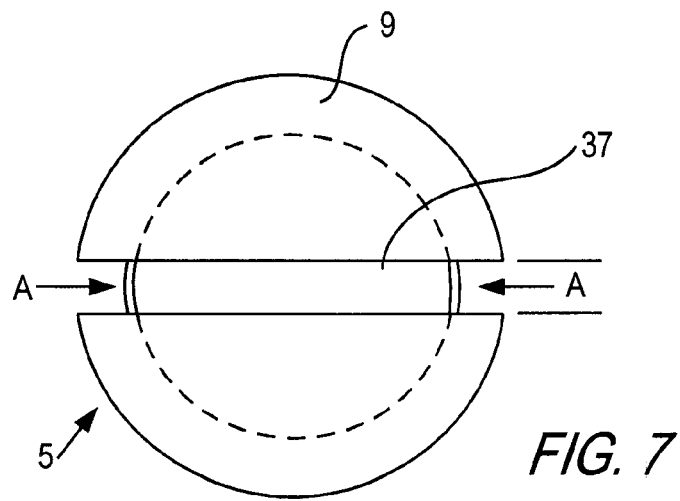
FIG. 7 illustrates an elevation view of a spheroidal-headed implant for the present invention, as shown in FIG. 1.
Figure 8:
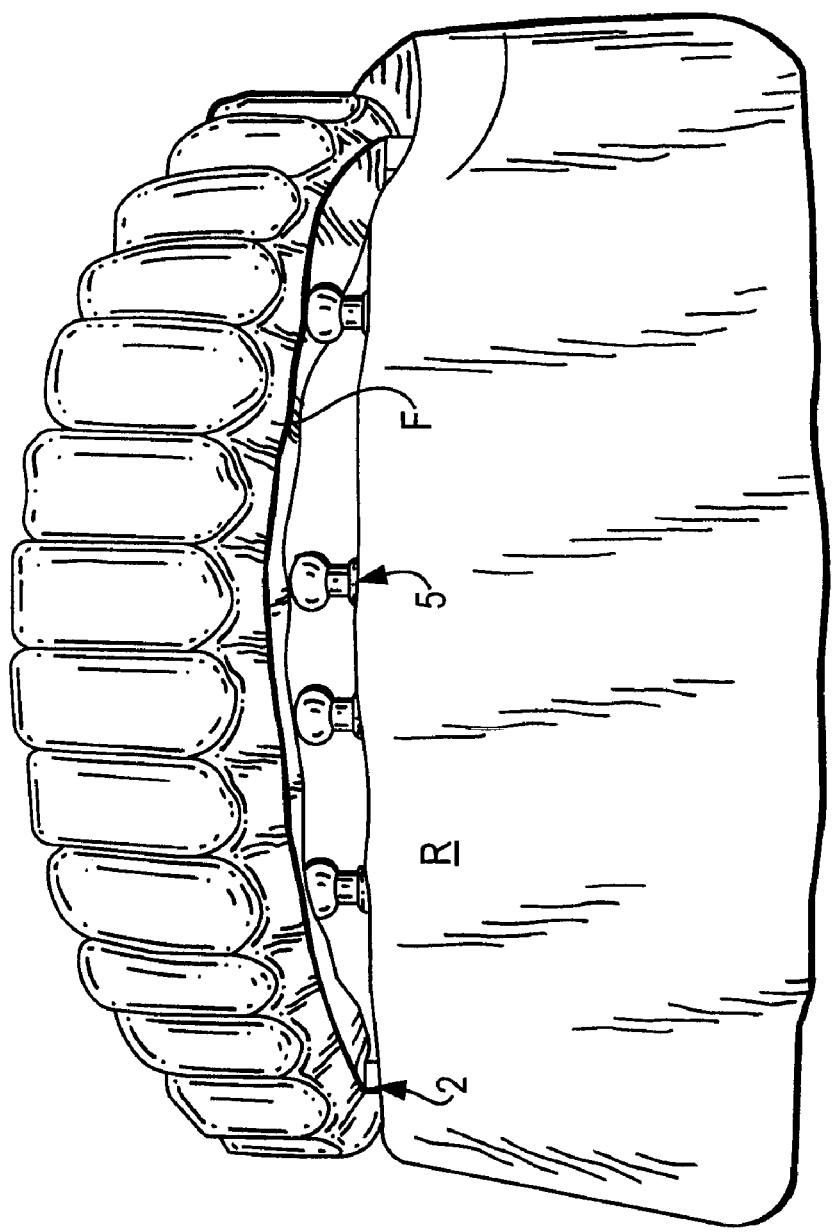
FIG. 8 illustrates a front view of a splint being applied to the jaw, over the holding implants.
Figure 9A:
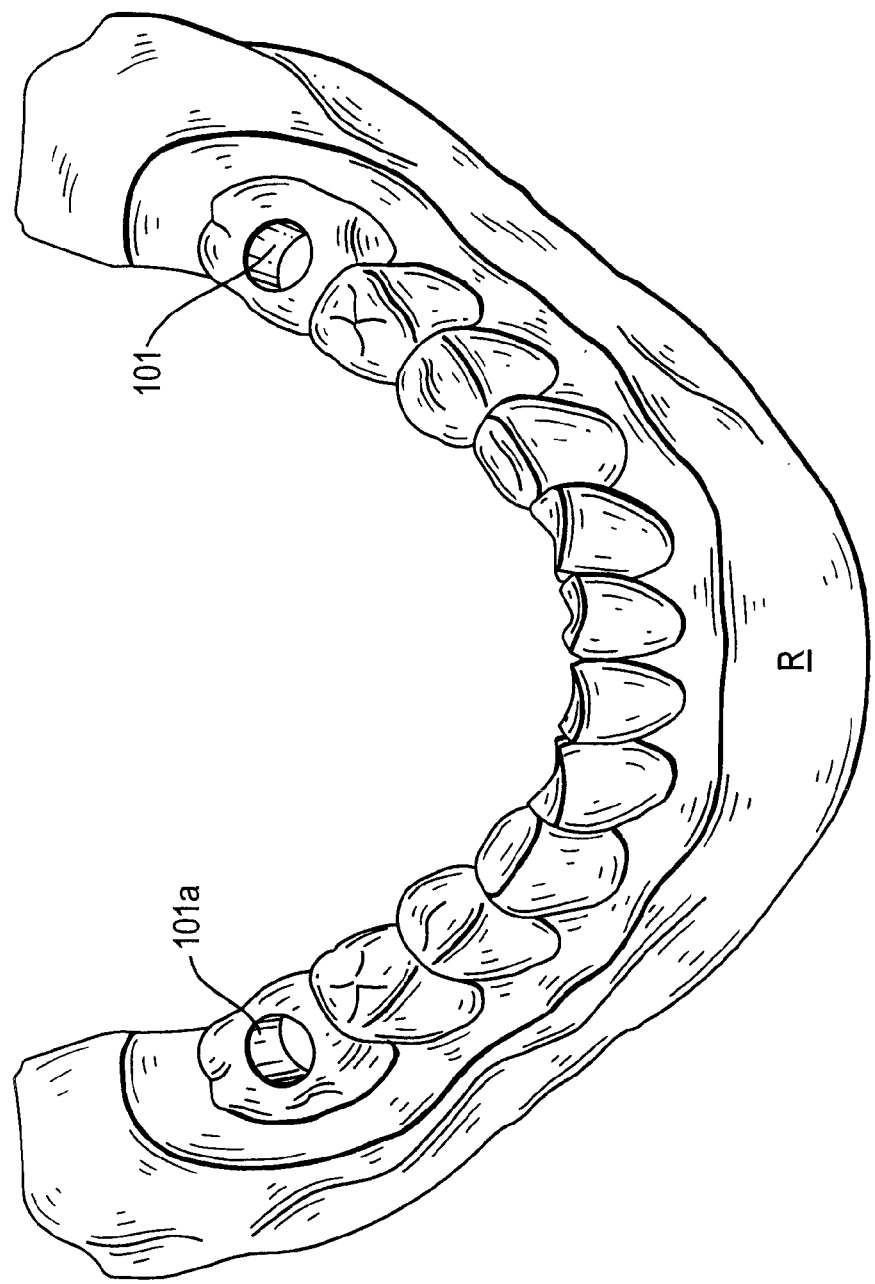
FIGS. 9A-I illustrate the procedure for forming a completed splint or dental prosthetic bridge in accordance with the present invention.
Figure 9B:
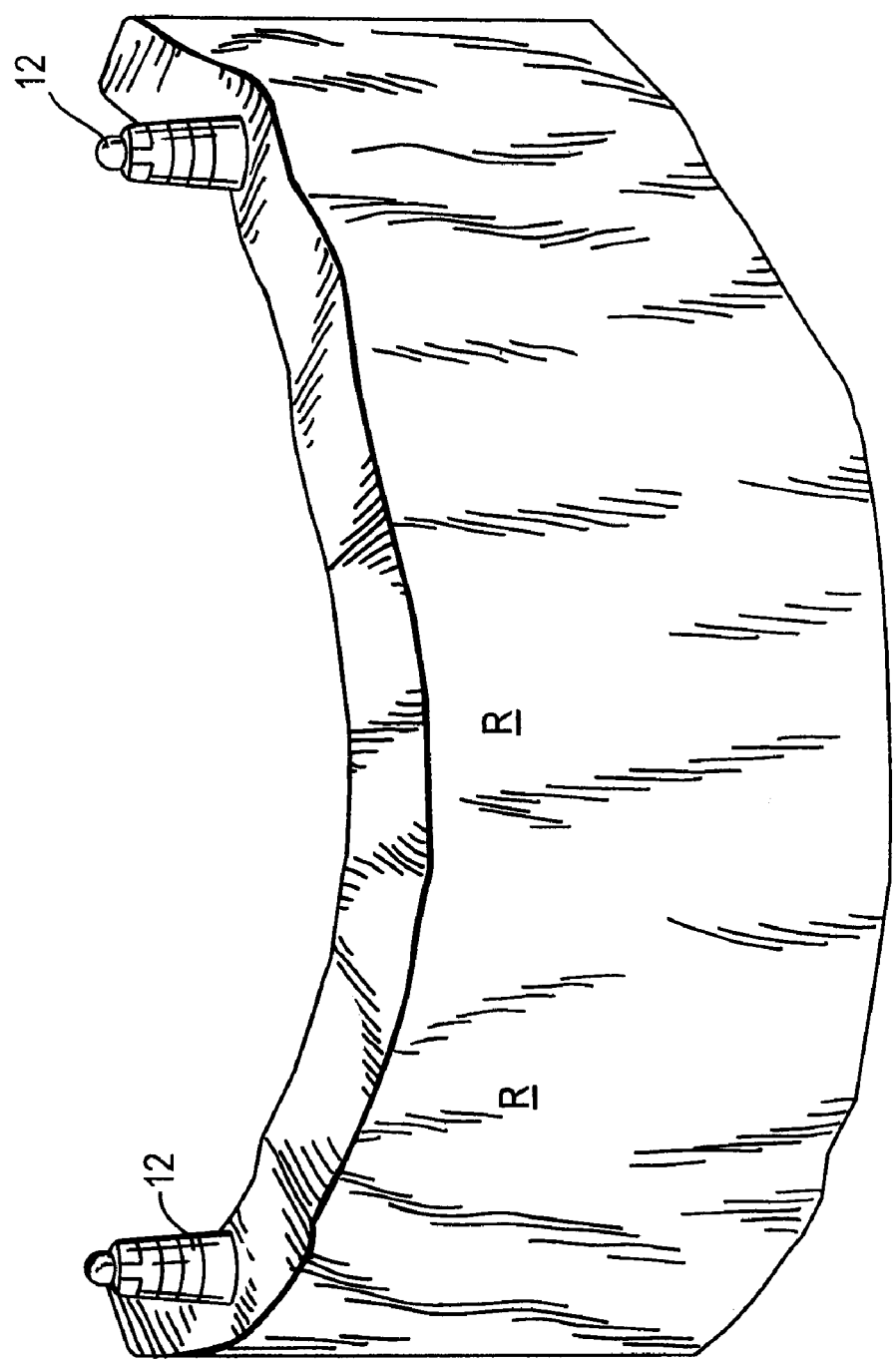
Figure 9C:
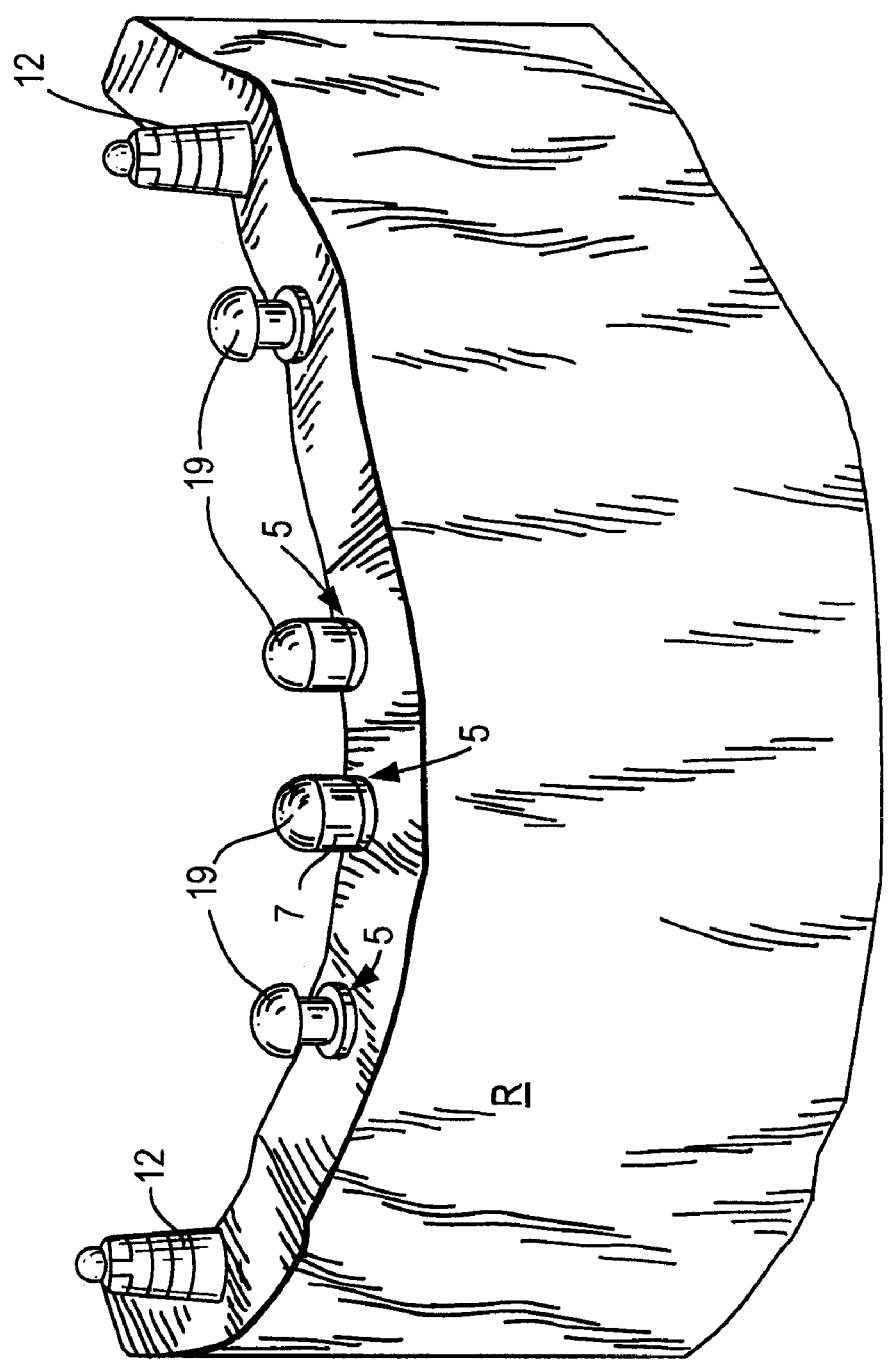
Figure 9D:
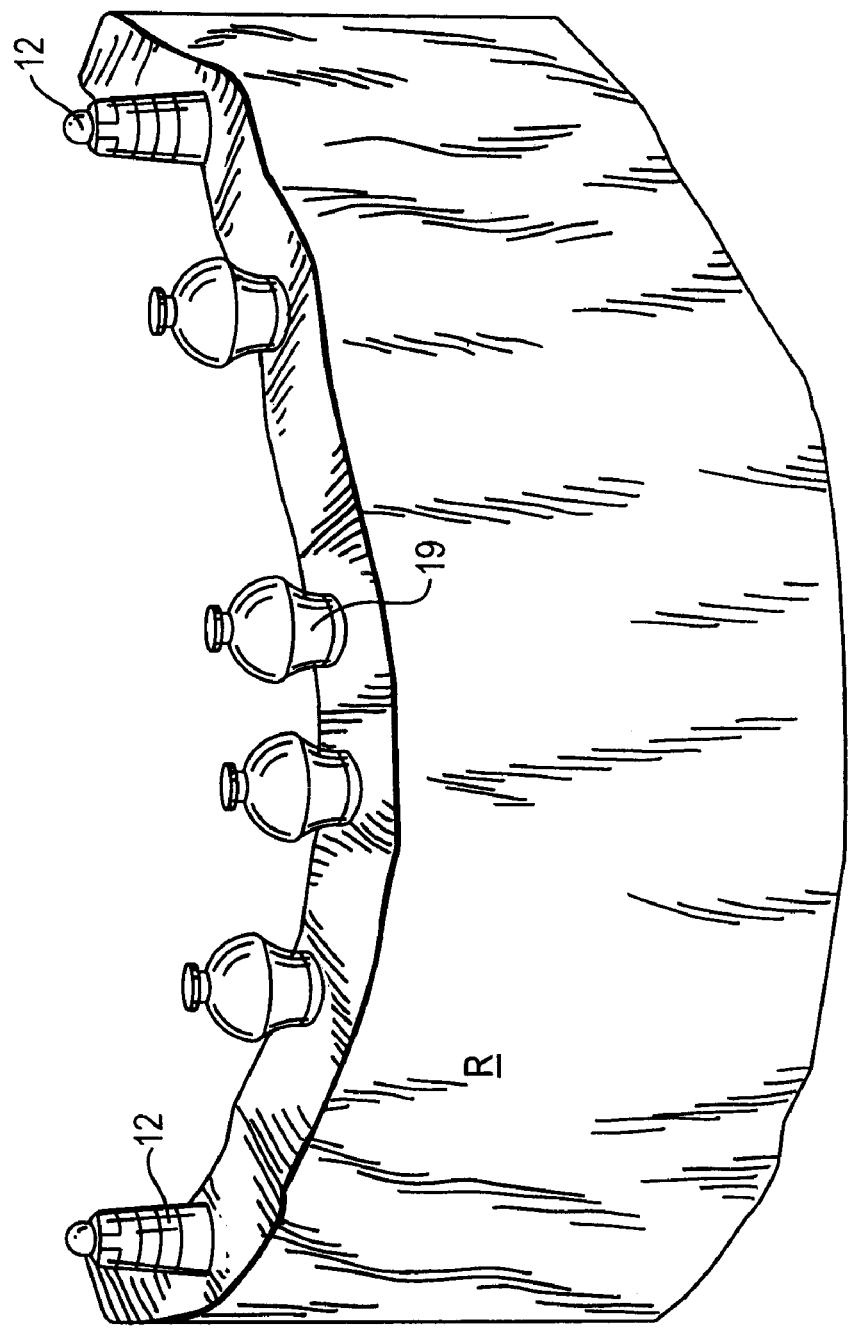
Figure 9E:
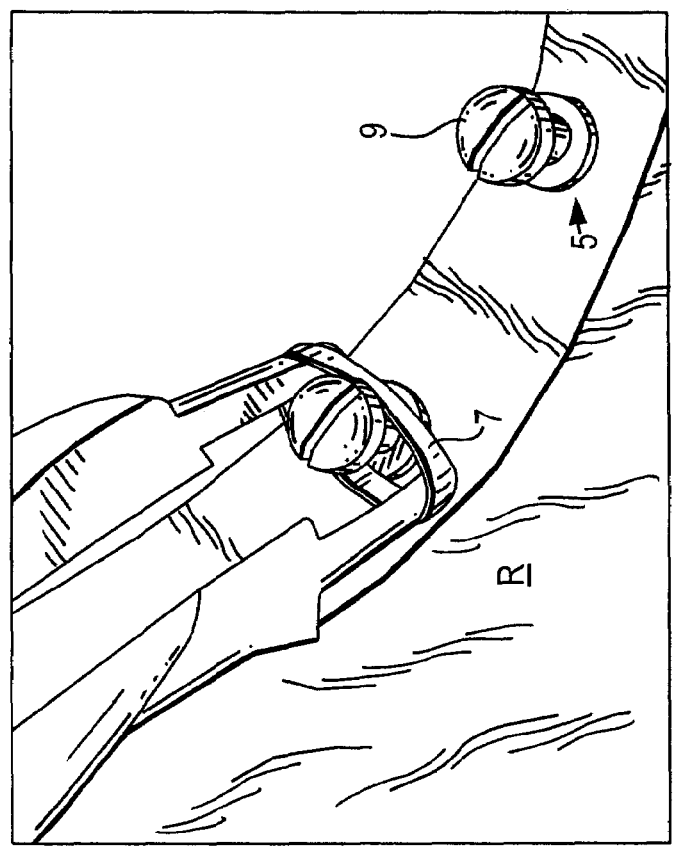
Figure 9E:
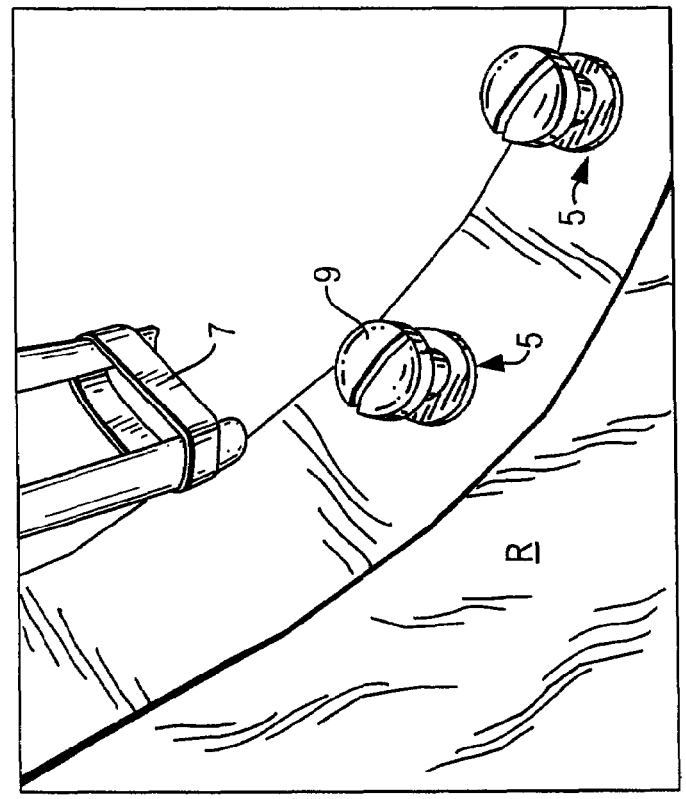
Figure 9F:
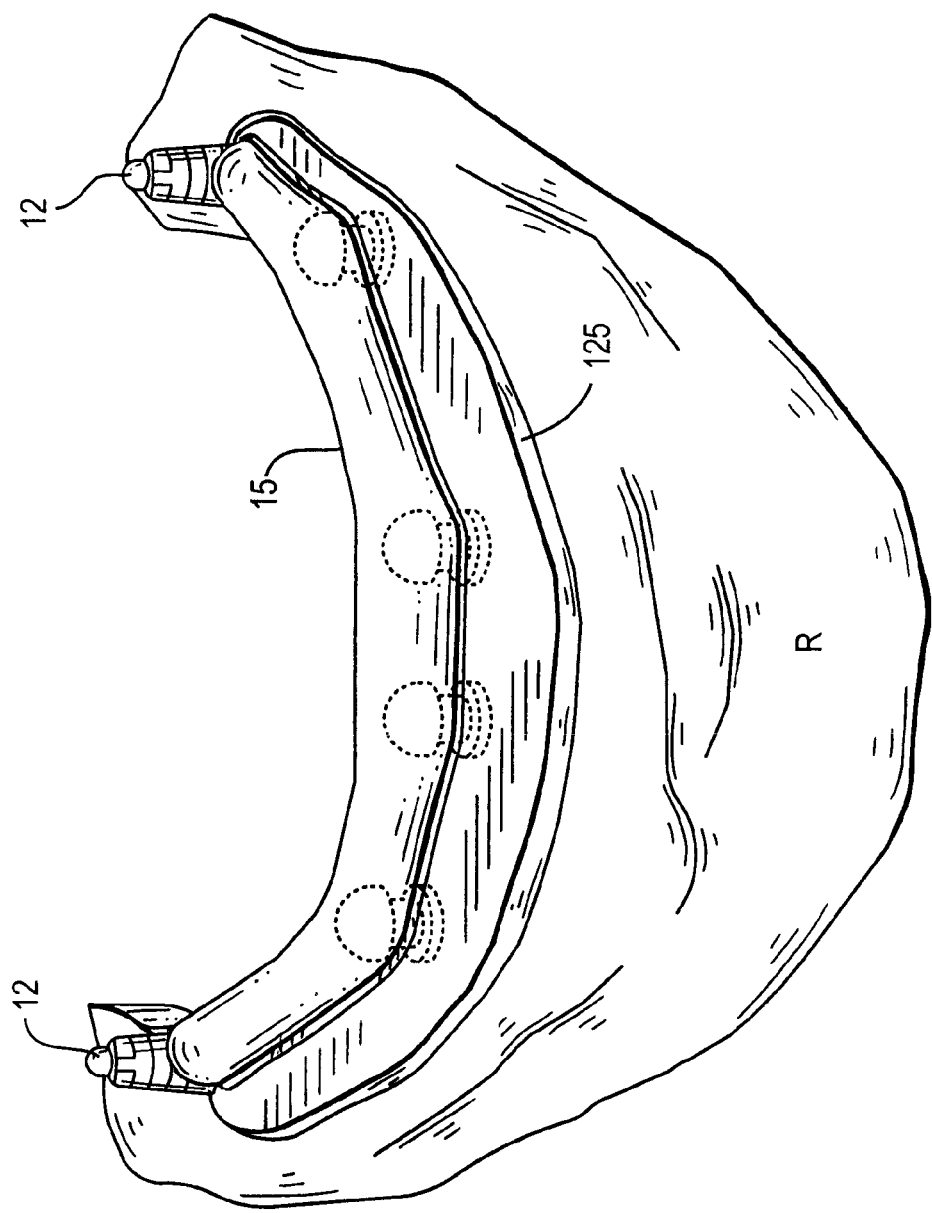
Figure 9G:
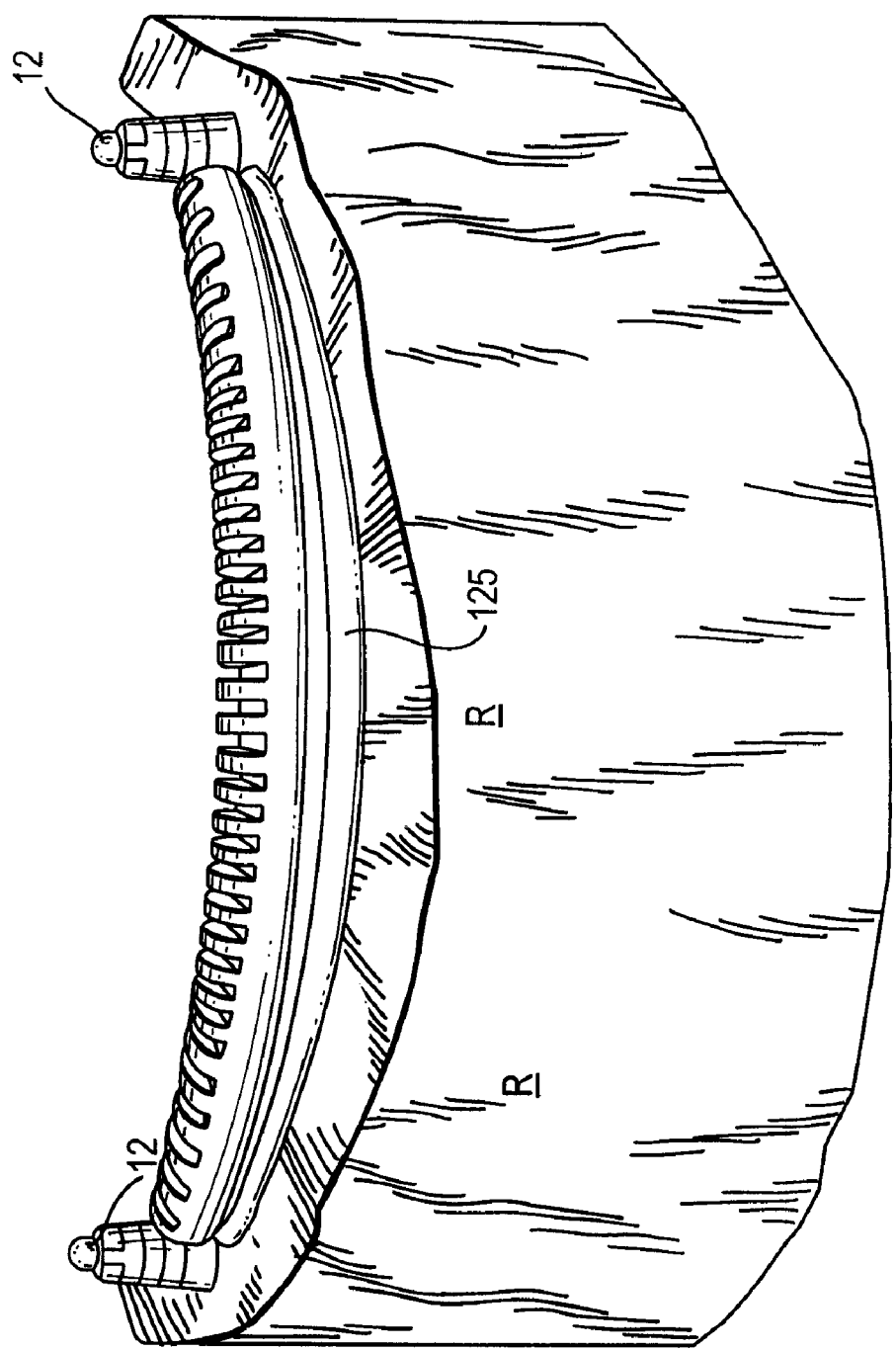
Figure 9H:
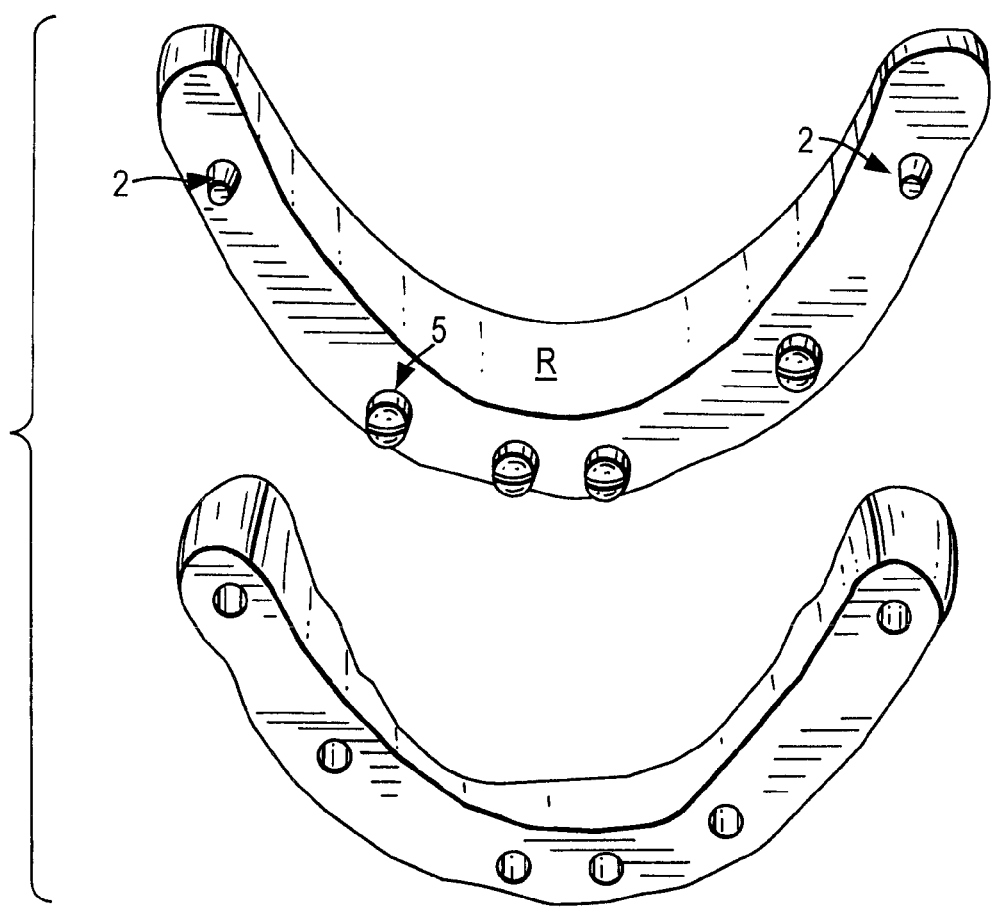
Figure 9I:
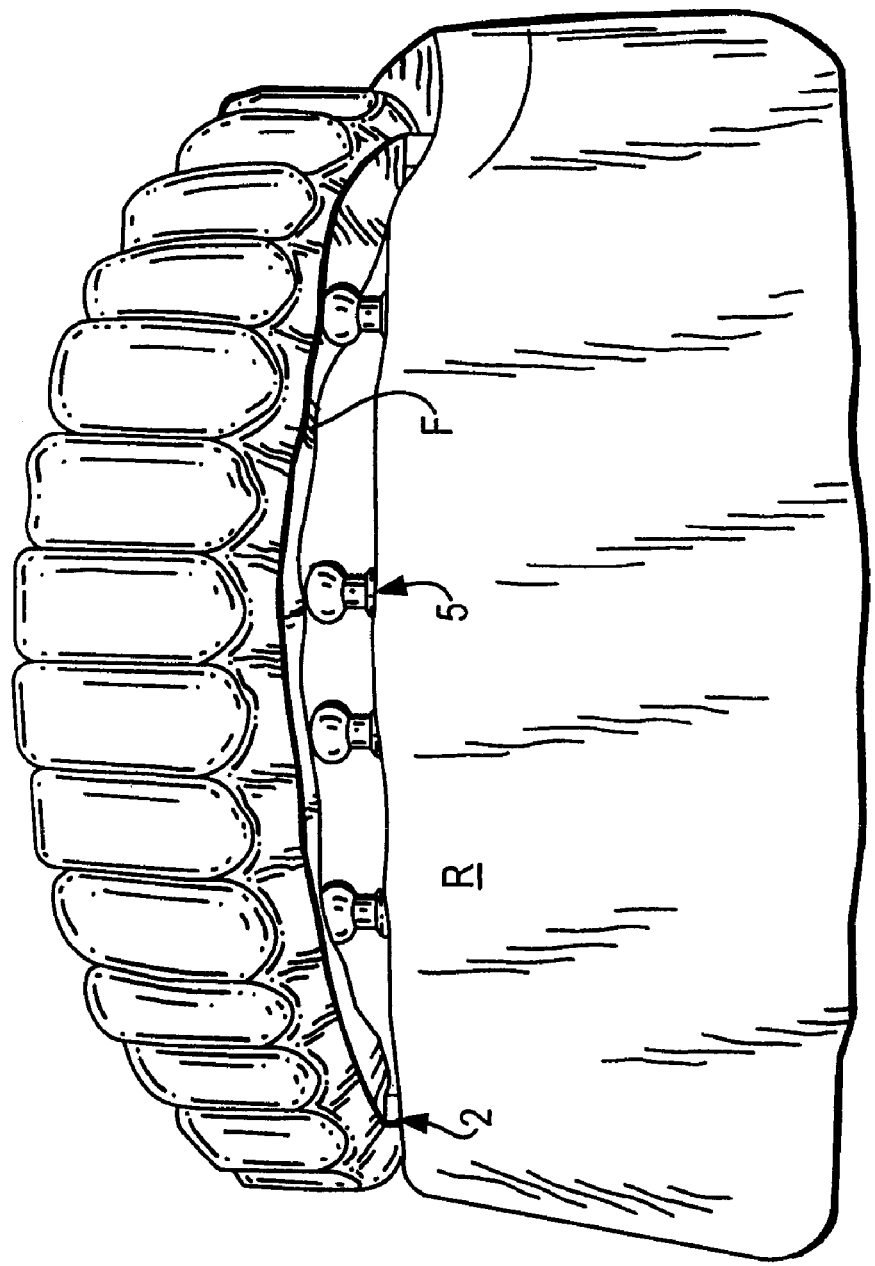

A model of a patient's jaw ridge R is shown in FIGS. 1 and 1a, including implanted into the jawbone ridge a pair of the guide, or indexing, pins 2 in the posterior-most portions of the model, and a series of implant screw type retention pins 5. Each of the retention pins in this embodiment, has a flattened dome-shaped, or spheroidal, head 9, and a narrower neck 10 and threaded shank 20, extending into the jawbone. Intermediate the shank and neck is a flange 22 having a distally facing platform 22A. The combination of the neck 10 and head 9 provides an undercut surface for retention and the platform 22A a firm support for the denture. In addition, closely surrounding the neck 10 there may be employed a removable elastic band 7, which can be utilized to vary the degree of any undercut effect by reducing or increasing the effective diameter of the shank to the needs of the patient.

Figure 11:
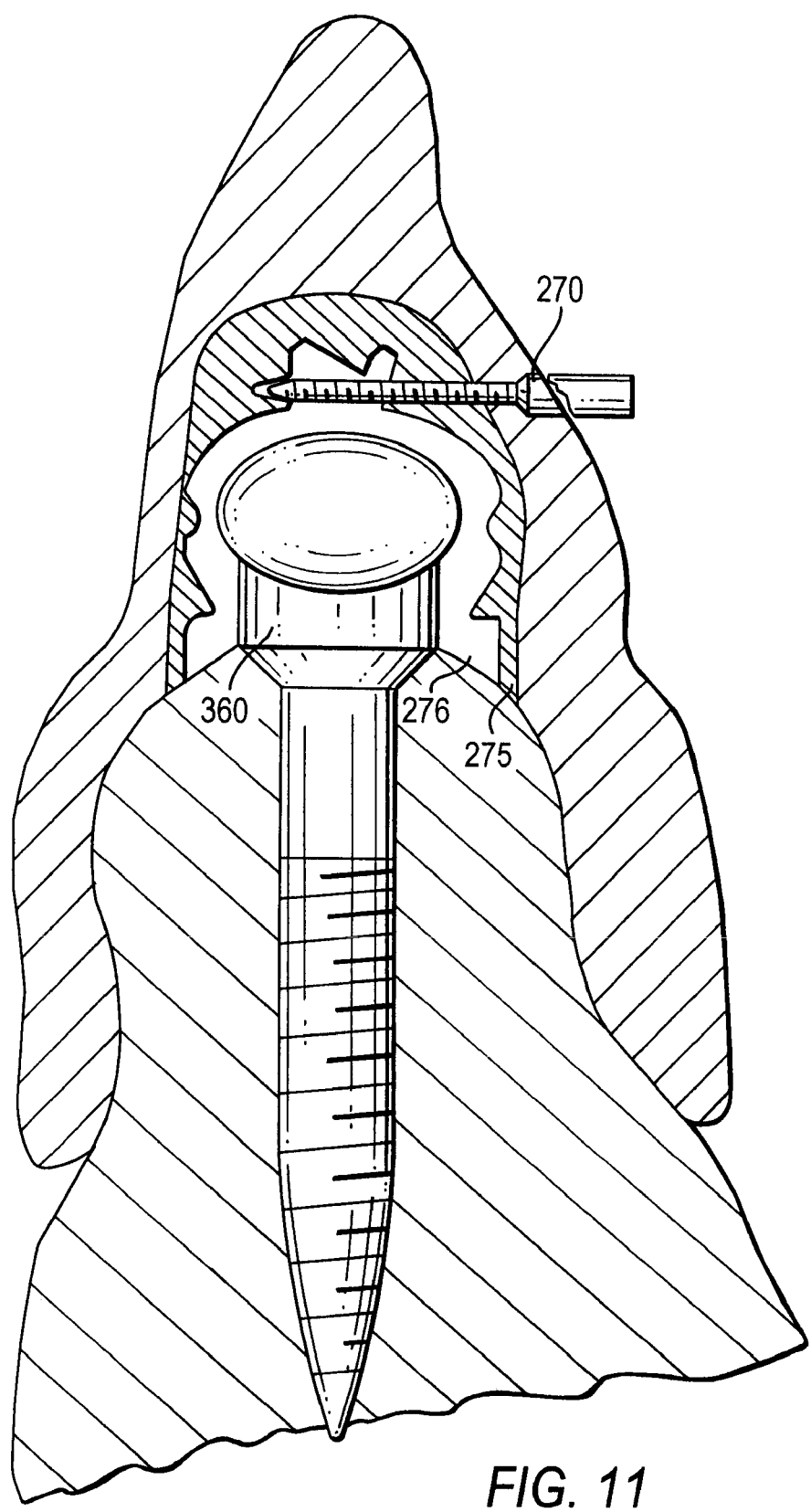
FIG. 11 illustrates a single tooth prosthesis anchored to an implant.
Figure 12:
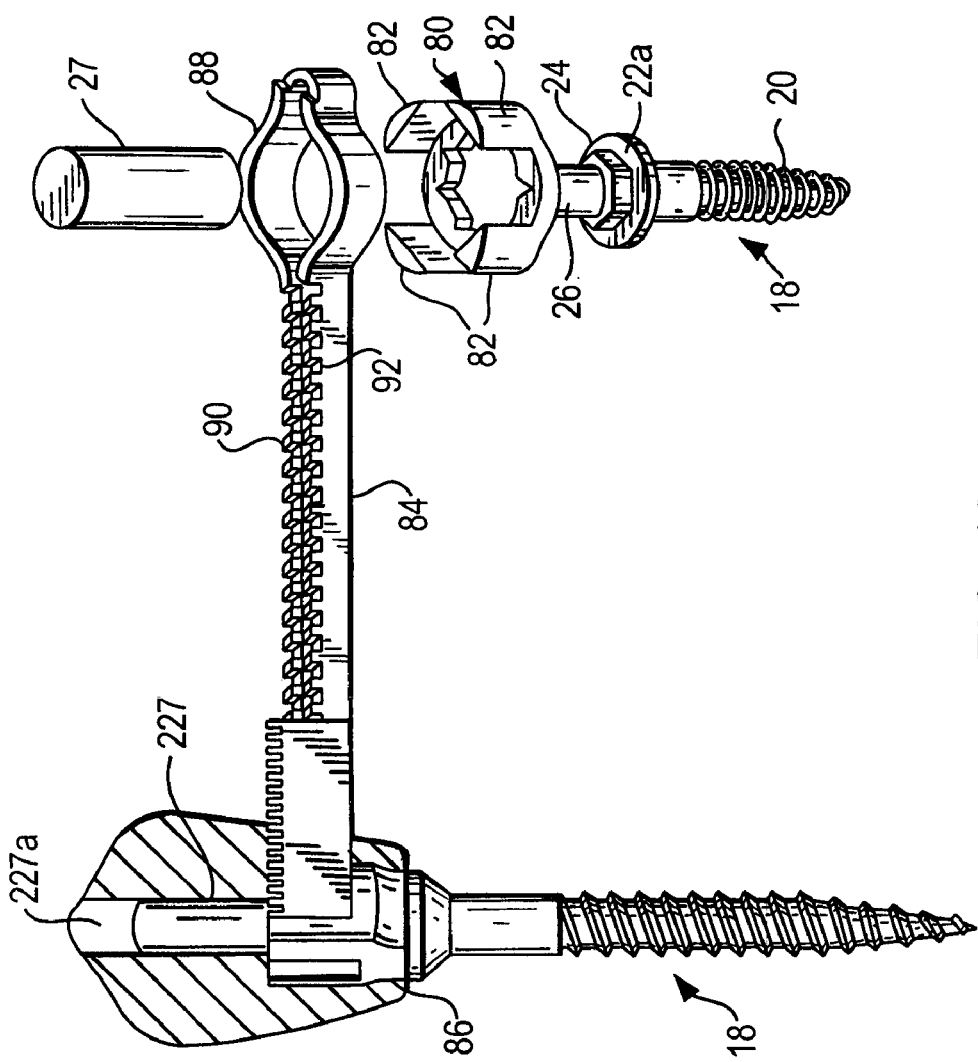
FIG. 12 illustrates the skeleton of a prosthesis foundation which is threadedly connected to the implants.

The spheroidal or ovoidal headed implant caps can be used for a single tooth prosthesis (FIG. 11) or as part of a bridge denture, with other such implants. As shown specifically in FIG. 12, and described more fully in the context of the Prior Case, another preferred embodiment of the holding implant screw 94, 18 has, at one end, a relatively long self-tapping threaded shaft 20. In use, an opening is made through any soft dental tissue, e.g., gums, overlying the jawbone, and the implant screw 18 is screwed into the hard dental tissue. The implant screw 18 has various advantageous features, such as a flange having a flat surface 22A on a first side adjacent to which modular components are positioned and supported, and having a tapered smooth portion 22B on a second side facing the dental tissue from which the threaded shaft 20 extends. The threads preferably do not extend the full length of the shaft 20, such that a substantially smooth, unthreaded portion is preferably present immediately adjacent the tapered portion 22B. In addition, this embodiment of the implant screw 18 includes a driving portion 24 which, in this example, is a flat polygonal extension, having a rectangular longitudinal cross-section. The driving portion 24 is adapted to engage a tool, such as a socket wrench bit. This is more fully set out in the Prior Case, incorporated herein. It is understood that the driving portion need not be in the specific shape shown, and may be polygonal concavity or extension, to engage compatible tools known in the art.

Figure 13:
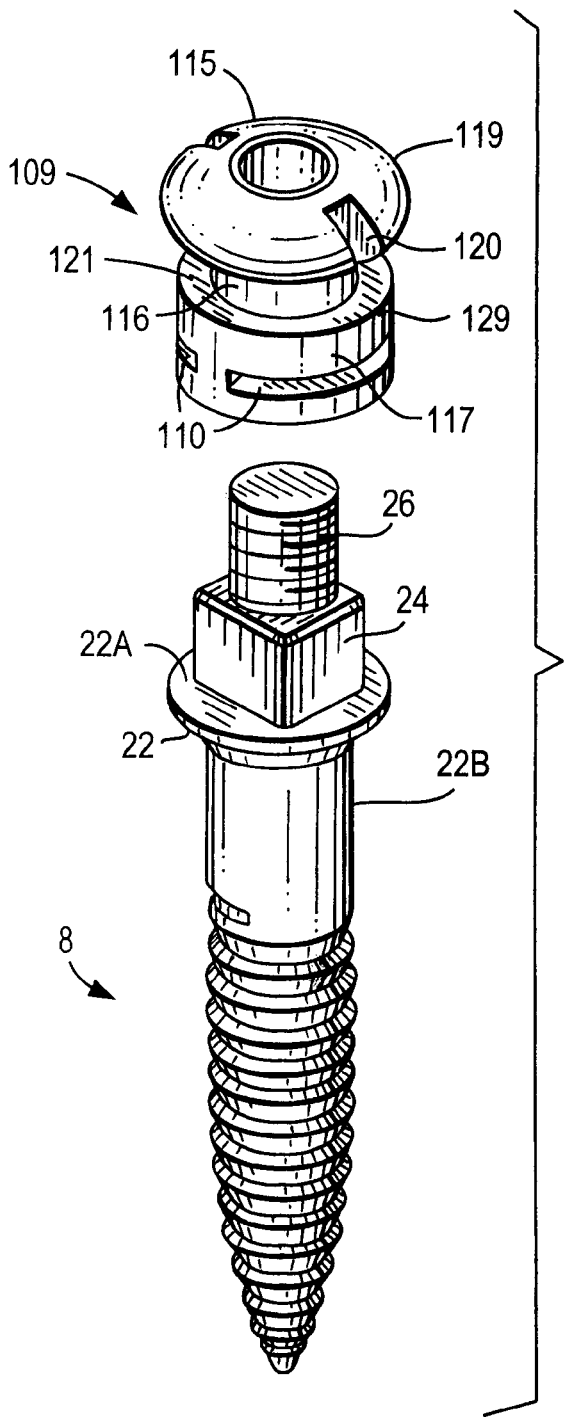
FIG. 13 is an exploded perspective view of a threaded dental implant and internally threaded upper locking cap.

The preferred embodiment of the slender holding implant screw 94, as shown in FIG. 13, includes at the protruding longitudinal end, prosthesis connecting member 26, for attaching modular prosthesis components thereto. As shown, the prosthesis connecting member 26 is externally threaded for receiving an internally threaded cap 109; for removably but rigidly connecting the implant screw to the splint.

Figure 14:
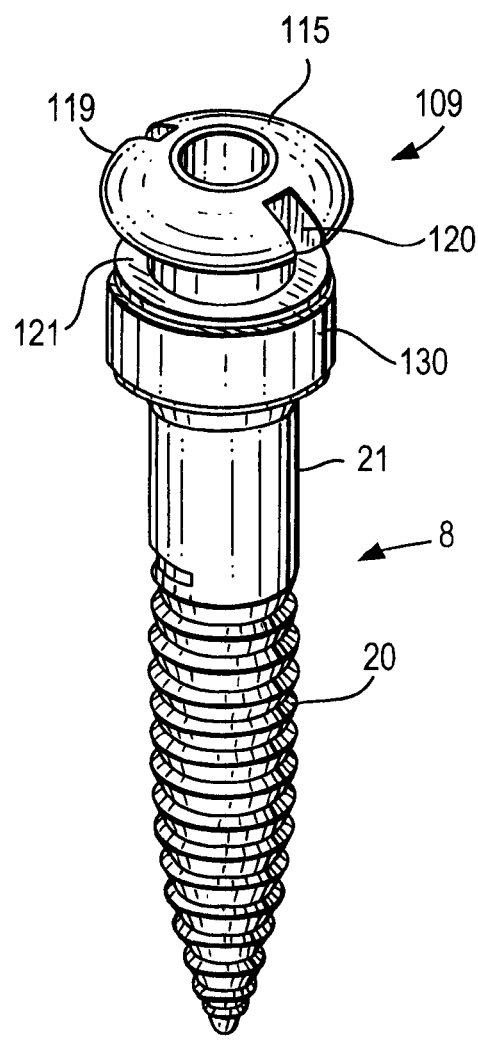
FIG. 14 is a perspective view of a threaded implant wherein the cap is threadedly connected to the implant and is in the process of being secured thereto utilizing a curable resin.
Figure 15:
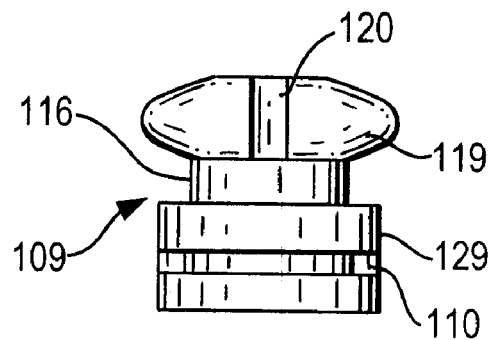
FIG. 15 is an elevational view of a spheroidal headed locking cap.
Figure 16:
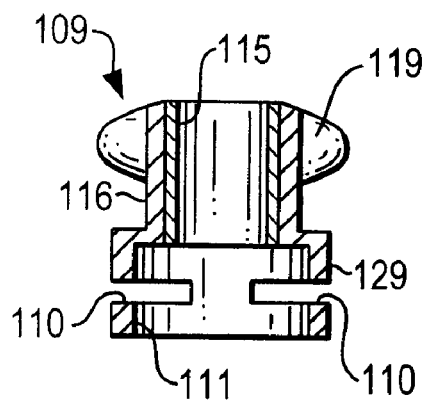
FIG. 16 is a partial cut away view of the locking cap of FIG. 15, taken along lines 16-16.
Figure 17:
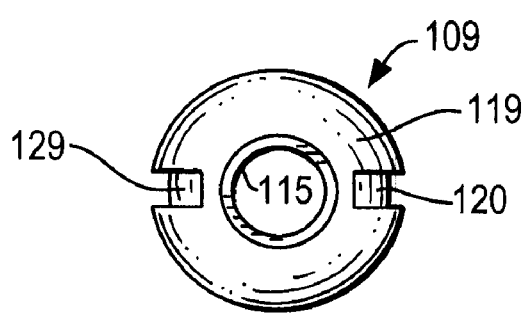
FIG. 17 is a top plan view of the spheroidal headed locking cap.

As shown specifically in FIG. 13, and described more fully in the "Prior Case", a preferred embodiment of the implant screw 8 has at one end a relatively long self-tapping threaded shaft 20 and an adjacent shorter smooth cylindrical shaft 21. A flange 22 is provided longitudinally adjacent the smooth portion of the shaft 21, distal of the threaded portion, and includes a smooth tapered portion immediately adjacent the shaft flowing outwardly to a flat surface substantially perpendicular to the axis of the shaft and facing away from the shaft. A driving portion having a substantially polygonal cross-section extends longitudinally from the flat flange surface portion 22. An externally threaded prosthesis connecting member 26 extends axially from the driving portion 24 in a direction away from the shaft 20. The non-adherent locking screw cap 109 of this invention is shown in a position in FIG. 13 adjacent the threaded connector 26, and in FIG. 14 screwed onto the threaded connector 26.

The locking cap 109 comprises an annular, open-ended skirt portion 129, having a generally cylindrical outer circumferential surface. A pair of circumferential apertures 110 are formed therethrough, so as to extend completely through the wall of the skirt 129.

At the distal end of the locking cap 109 is a substantially spheroidal head portion 119 having radial, transversely extending slots 120 formed at diametrically opposed edges of the circumference of the spheroidal head. A narrower neck portion 116 is located intermediate the top of the skirt portion 129 which is defined by a relatively flat surface 121, and the spheroidal head 119. A central opening, defined by an internally threaded wall surface 115 extends completely through the spheroid head 119 and the neck portion 116, to the interior of the skirt portion.

Figure 18A:
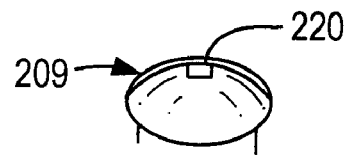
FIG. 18A-C are elevational front and side views, respectively, and a top view, of an ovoidal locking cap.
Figure 18B:
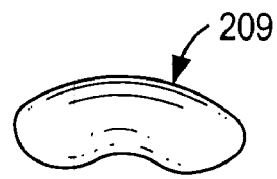
Figure 18C:
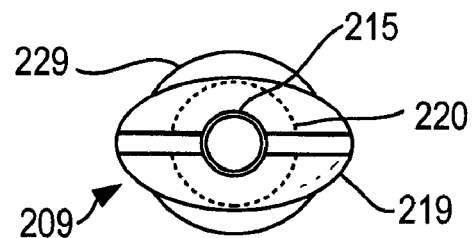

An alternative locking cap 209 is shown in FIGS. 18A-C. At the distal end of the locking cap 209 is a substantially ovoidal head portion 219 having slots 120 preferably extending along the major circumference of the ovoidal head, as shown. The remaining aspects of this cap are as described above.

The locking caps 109, 209 of this invention are preferably molded from a polymer of the types commonly used for placement in the mouth, by dentists, such as the polyacetal resin Delrin, utilizing either co-polymer grades or homopolymer grades. Other useful materials include dental grades of nylon or polysulfone. Other suitable dental resins having the desired mechanical strength may also be utilized.

The relatively soft locking cap 109 made of a polymeric material is preferably used at least during the preliminary period after the implant is first affixed, when it is desired to provide an immediate replacement or splint to both hold a plurality of such implants in place and to provide the patient with at least an immediate replacement for the missing teeth, even though it is not one that may be maintained on a permanent basis. After the implants and bone have healed and become firmly secured, the permanent prosthesis can then be fitted. As the fitting of a permanent prosthesis often requires several trials, when the prosthesis must be removed, refitted and replaced, the use of a hard metal cap during this period could result in some damage to the metal implants. By utilizing the relatively soft resin cap, the likelihood of any damage occurring to the implant, from a cross threading or the like, is greatly reduced, if not wholly eliminated.

To further enhance the effectiveness of these caps, and to avoid their coming loose during this period, the caps can be initially filled with a curable dental resin in the cup formed by the skirt, preferably of the auto-cure or light cure type, and the cap is then applied to the threaded top portion of the implant and screwed down, while the excess resin from the skirt portion is squeezed out the top of the cap through the opening defined by the surface 115.

As noted, the apertures 10 can be covered by a removable silicone sleeve 130 during curing, having sufficient elasticity to be able to be readily removed after the resin is set, if desired. The dental resin is generally not adherent to the silicone so the resin does not interfere with the removal of the sleeve. Any excess uncured resin which exudes from the top of the cap during the process of its being screwed on to the implant can be readily wiped-off before it hardens.

When the resin in the skirt is hardened, it surrounds the polygonal drive member 24 and extends into the apertures. This prevents inadvertent rotation of the cap when subjected to various stresses in the mouth. However, when the cap and resin are subjected to torque by the application of e.g., the U-shaped driver, on the slots 120,220, the hardened resin in the apertures will press against the narrow portions 117 separating the apertures; these narrow portions in the skirt 117 are relatively weak, so that when torque is applied to the head of the resin cap the narrow portions with rupture. The cured dental resin, within the apertures of the skirt, pressing against these narrow portions between the apertures, will cause them to rupture upon the application of a reasonable torsional force, e.g. by utilizing a "U" shaped driver in the opposing slots 120,220. The intermediate wall portions 117 can be further weakened by machining out some material so they are not as thick in cross-section as the remaining portion of the skirt wall 129. The top portion of the cap can be removed when it is unscrewed. The lower skirt surrounding the driving portion 24 can be readily lifted out and removed, exposing the exposed threaded connection 26, for attaching a new cap when the prosthesis is replaced by the dentist. This process can be repeated several times as needed during the trials and fittings of a customized prosthesis, without likelihood that the implant will be damaged.

Prior to initially forming the splint, of whichever form, a mold of the mouth showing the locations of the upper ends of the implants and their shape, together with any indexing element 80 present on each implant, is made using the usual dental impression material. A denture prosthesis can be prepared from this mold, by known procedures, which will locate the implant tops extending through the dental prosthesis. The concavity formed by the posterior indexing implants should be expanded to a larger opening to leave room for the jacket insert to be attached to the denture. This initial foundation, formed from a relatively hard dental resin, is then treated to remove material from the concave portion formed around the jaw ridge, to permit the molding and/or insertion of a softer more resilient dental resin liner, if desired.

This is not a part of this invention and merely provides the context for its use. This context is described more fully in a prior published application by the applicant (U.S. Patent Publication 2004/0166476-A1).

The use of the caps of this invention does not interfere with conventional molding techniques for dentures and, thus, allows dentists and dental laboratories to continue with their usual practice when forming a permanent denture prosthesis.

The above disclosure sets forth preferred embodiments of the present invention. Only the following claims fully define the invention:

The following invention is claimed:

1. A locking cap for a rigid dental implant, the locking cap being formed of a material that is rigid but relatively softer than the material forming the dental implant, the locking cap comprising at one end a substantially spheroidal or ovoidal head portion having a driver gripping surface formed therein; a substantially annular skirt portion at the second end and comprising an annular wall defining a plurality of slotted apertures extending therethrough, separated by relatively thin and structurally weak sections of the annular wall, the slotted apertures extending circumferentially along the annular wall; and an axially extending intermediate portion, between the skirt and head portion, having a diameter smaller than the outer diameter of the spheroidal head or of the skirt portion or major diameter of an ovodial portion and extending longitudinally therebetween; the intermediate portion having an axial bore extending therethrough and having an internal circumferential surface;

the internal circumferential surface within the intermediate member is threaded; and wherein the locking cap can be threadedly connected to an implant having an outwardly extending threaded connector.

2. The cap of claim 1 wherein the head portion is substantially spheroidal and the structurally weak sections extend in toto along not more than 20% of the circumference of the skirt portion.

3. The cap of claim 1 wherein the structurally weak sections have a cross-section thinner than the cross-section of the remainder of the skirt portion.

4. The cap of claim 1 further comprising interior wall surfaces defining a central opening extending through the spheroidal head and the intermediate portion opening into the volume within the annular wall of the skirt.

5. The locking cap of claim 1, wherein the material of construction is selected from the group consisting of polyacrylics or silicones.

6. A method of fitting in situ a resiliently lined rigid prosthetic denture, of the type removably secured to permanently implanted dental support posts embedded into a patient's jaw, where the support posts each include a shank secured into the patient's jaw and a threaded interconnectable portion extending outwardly longitudinally from the shank and beyond the patients jaw surface, the method comprising the steps of molding a denture prosthesis foundation, to form a dental prosthesis including openings therethrough, for each outwardly extending implant threaded interconnectable portion, and a concave portion intended to fit over and around the jaw ridge, the foundation being formed from a relatively hard dental resin, a portion of the hard dental resin defining the concave portion is removed to provide space for the insertion of, and the molding of, a softer more resilient dental resin liner in the concave portion, in situ, on the jaw ridge, inserting a curable softer more resilient dental resin into the concave portion, removably placing the denture foundation onto the jaw ridge in which is a series of implanted posts in the mouth of the patient, and allowing the resilient resin to cure and set so as to form a suitable seal between the cured resilient resin and the sides of the jaw ridge when the prosthesis foundation is threadedly removably secured to the jaw, and threadedly removably securing the foundation to each post with a locking cap in accordance with claim 1, to removably but sealably secure the foundation in the mouth.

7. The method of claim 6, wherein the locking cap includes a substantially spheroidal head portion, and further comprising filing the annular skirt portion with a curable resin which is selected from the group of auto-curing and light-curing polyacrylic and epoxy silicone polymers.

* * * * *